(12) United States Patent
Giusti et al.

(10) Patent No.: US 8,575,334 B2
(45) Date of Patent: Nov. 5, 2013

(54) HIGH-PURITY FRACTIONATION OF ANTHOCYANINS FROM FRUITS AND VEGETABLES

(75) Inventors: Maria Monica Giusti, Columbus, OH (US); Jian He, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 12/847,106

(22) Filed: Jul. 30, 2010

(65) Prior Publication Data

US 2012/0029178 A1 Feb. 2, 2012

Related U.S. Application Data

(63) Continuation of application No. PCT/US2009/033127, filed on Feb. 5, 2009.

(60) Provisional application No. 61/063,763, filed on Feb. 8, 2008.

(51) Int. Cl.
*C07H 1/06* (2006.01)
*C07H 1/08* (2006.01)

(52) U.S. Cl.
USPC .......................................... 536/128; 536/4.1

(58) Field of Classification Search
USPC ......................................................... 536/128
See application file for complete search history.

(56) References Cited

PUBLICATIONS

Castillo-Munoz et al., Journal of Agricultural and Food Chemistry, 2007, 55, 992-1002.*
He, Jian, a dissertation retrieved on May 23, 2012 from Internet <http://etd.ohiolink.edu/view.cgi/He%20Jian.pdf?osu1222108733>, published in 2008, 184 pages.*
Houbiers et al., J. Phys. Chem. B, 1998, 102, 3578-3585.*

* cited by examiner

*Primary Examiner* — Elli Peselev
(74) *Attorney, Agent, or Firm* — MacMillan, Sobanski & Todd, LLC

(57) ABSTRACT

Disclosed is a method for separating anthocyanins depleted in phenolic mixture content from fruits or vegetables feedstock containing anthocyanins and phenolic mixtures. The first step is to contact the feedstock with a cation-exchange resin at low pH for a time period effective for the resin to selectively bind with the anthocyanins. Next, the non-bound phenolic mixture is separated from the resin for recovery. The bound resin is subjected to solvent wash to release the anthocyanins for recovery.

15 Claims, 5 Drawing Sheets

HIGH-PURITY FRACTIONATION OF ANTHOCYANINS FROM FRUITS AND VEGETABLES

CROSS-REFERENCE TO RELATED APPLICATIONS

This application is a continuation of PCT application number PCT/US09/033127, filed 5 Feb. 2009, which claims the benefit of U.S. provisional patent application No. 61/063,763, filed on 6 Feb. 2008.

BACKGROUND

Anthocyanins, a class of polyphenols, are responsible for the blue, red, and purple color in many fruits and vegetables. Increasing evidence shows that anthocyanins are potent antioxidants and are associated with protective effects against many coronary diseases such as cancer, cardiovascular diseases, and even obesity. Interest on the use of anthocyanins, as alternatives to synthetic colors in foods, has increased and many researchers are continuing investigating their potential health benefits. Obtaining high-purity anthocyanins is essential for such research. Many bioassays on anthocyanin-rich commodities would not be feasible without eliminating bioactive impurities that obscure interpretation of results. In the food colorant industry some potential low-cost anthocyanin sources could not be commercialized because of co-extracted adverse flavor or even toxic chemicals. Current anthocyanin separation methods are not practical to achieve high purity at reasonable cost. In this study we attempted to develop a new technique that can substantially elevate anthocyanin purity using a low-cost and high-throughput procedure.

To date there have been over 540 naturally occurring anthocyanins identified. Unfortunately, there are only a limited number of pure standards commercially available at high cost. Therefore, many biological studies are performed using crude anthocyanin extracts from fruits and vegetables. Isolation methods range from simple water or organic solvent extraction to various forms of chromatography. Solid-phase extraction (SPE) methods currently are the most commonly used, due to a balance of efficiency and cost. However, such methods normally rely on hydrophilic or hydrophobic interactions between the sorbent and the analyte, which would inevitably allow for a broad spectrum of plant constituents to mix into the anthocyanin fraction. The impurities, usually phenolic compounds, are likely to have biological effects, as well, and therefore become confounding factors in bioassays. Thus, explanation of anthocyanin bioactivity could be vague, and results from different labs could be hardly comparable given the different isolation methods employed.

Broad Statement

Disclosed is a method for separating anthocyanins depleted in phenolic mixture content from fruits, vegetables, and flowers (herein, collectively, plant tissue) feedstock containing anthocyanins and phenolic mixtures. The first step is to contact the feedstock with a mixed-mode cation-exchange resin at low pH for a time period effective for the resin to selectively bind with the anthocyanins and other phenolics. Next, the non-anthocyanin phenolic mixture is selectively separated from the resin by solvent wash for recovery. The resin is subjected to additional solvent wash to release the anthocyanins for recovery. For human consumption, the solvent should be a food-grade solvent, i.e., a solvent permitted by regulation for human consumption. For animal (excluding humans) consumption, the solvent should be an animal-grade solvent, a solvent permitted by regulation for animal (non-human) consumption.

Advantages of the process disclosed herein include the successful use of mixed-mode cation exchange for anthocyanin purification, which is believed to function due to the use of a combination of cation exchange and hydrophobic interaction. Another advantage is the achievement of higher purity than current methodology for fractionation of anthocyanins at comparable cost. A further advantage is the ability to purify the same amount of anthocyanins using much less organic solvents than prior purification processes with less processing time being required. The lifetime and consistency of this polymer-based resin also exceed the conventional silica based resin and therefore result in reduced cost and improved reproducibility.

DETAILED DESCRIPTION

Figure 1:
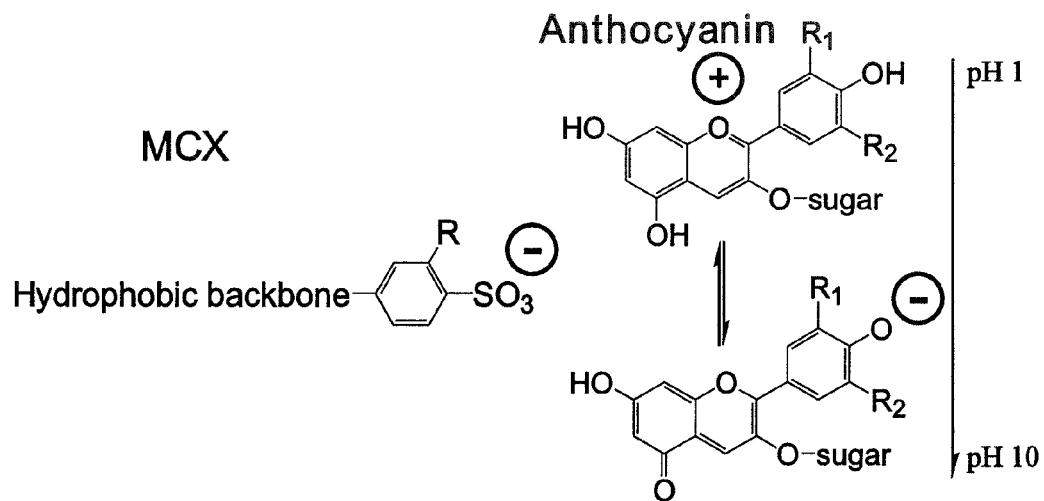
FIG. 1 illustrates the positive charge on anthocyanin flavylium cation at low pH.

A novel means for anthocyanin separation based on a cation-exchange mechanism is disclosed herein, taking advantage of the positive charge on anthocyanin flavylium cation at low pH (see FIG. 1), a unique characteristic not found in most other plant constituents.

The resin reported herein is a modified divinylbenzene-vinylpyrrolidone copolymer with a hydrogen atom on benzene substituted by a sulfuric group (supplied by Waters Corporation). The structure is displayed in FIG. 1A.

A unique property of anthocyanins, molecule protonation at low pH, was explored as basis for separation using a novel cation-exchange/reversed phase combination technique, the Oasis® MCX SPE column, and developed water/organic buffer mobile phases to selectively separate anthocyanins. Crude extracts of bilberry, black currant, black raspberry, blueberry, chokeberry, elderberry, grape, purple carrot, purple corn, radish, red cabbage, and strawberry, as representative anthocyanin sources, were purified with this technique and compared to 3 commonly used solid-phase extraction techniques: Sep-pak® $C_{18}$, Oasis® HLB, and Sephadex® LH-20 columns. Purified anthocyanin fractions were analyzed with High Performance Liquid Chromatography (HPLC) coupled to Photodiode Array (PDA) and Mass Spectrometry (MS) detectors and evaluated with a Fourier Transform Infrared (FTIR) Spectroscopy. Purity and yield of anthocyanins were analyzed with SPSS using nonparametric counterpart of ANOVA and Student's t-test.

The UV-visible chromatograms quantitatively demonstrated that the disclosed technique successfully increased eight of the twelve tested anthocyanin sources to remarkably high purity (99.0%-99.9%). Four other sources also were significantly ($P<0.05$) improved, as compared to conventional methods at comparable cost. The new method efficiently removed the majority of non-anthocyanin phenolics, with which all the conventional methods had been ineffective. As complimentary analytical tools to the UV-visible chromatograms, mass spectrometry and infrared spectroscopy semi-quantitatively confirmed extensive reduction of impurities with the disclosed new method. The overall yield by the new method (93.6%±0.55%) was not significantly different ($P>0.05$) from the $C_{18}$ method (93.8%±0.36%), but considerably higher than the other two methods. Due to strong ionic interaction, the disclosed methodology also achieved several folds higher column capacity than others, as measured by break-through volume, resulting in the highest throughput and least use of organic solvents.

The introduction of a strong cation-exchange mechanism revolutionized anthocyanin separation methodology to drastically increase the purity and efficiency while maintaining excellent yield. Therefore, it could become a rapid, low cost, and high throughput method to provide high-purity anthocyanins in research labs for minimized interference from other compounds. Employing alternative non-toxic solvents, this method can provide highly purified anthocyanins for animal studies and clinical trials with respect to the health benefits of anthocyanins. A scale-up production may provide the food colorant industry and nutraceutical industry a practical way to separate high quality anthocyanins, even from industry by-products that naturally contain adverse flavor or low concentration of toxic compounds.

From another perspective, the disclosed method also can be employed to produce phenolic mixtures relatively free of anthocyanins. In many cases, phenolic compounds, such as, for example, grape tannins, are the target molecules being studied and researchers desire to remove anthocyanins from such phenolic mixtures. Removal of anthocyanins from phenolic mixtures aids in improving biological and chemical tests of such phenolic mixtures.

EXAMPLES

Materials and Methods

Crude extracts of chokeberry and purple corn, as representative anthocyanin-rich sources, were loaded onto a strong cation exchange Oasis® MCX SPE cartridge. After washing with 2 volumes of 0.1% TFA, the phenols were collected by 2 volumes of methanol (0.1% TFA). Then, anthocyanins were eluted with 1 volume of methanol and 1 volume of water/methanol (40:60, v/v), both with 1% $NH_4OH$. The combined eluate was immediately mixed with an aliquot of formic acid to bring the pH to <2, briefly evaporated in a Büchii rotovapor at 35° C. to remove organic solvent, and then brought to known volume with water.

Purified phenolic and anthocyanin fractions from Sep-pak® $C_{18}$, Oasis® HLB, and Sephadex® LH-20 SPE cartridges were obtained using reported optimum conditions or slightly modified procedures. All the fractions with 8 replications were analyzed using a HPLC equipped with a PDA detector and a single quadrupole electron spray ionization (ESI) MS detector. Concentrations of anthocyanins and total phenols were calculated by area under the curve (AUC) in the 510-530 nm and the 250-700 nm max-plots respectively. Purity was calculated by dividing the AUC of anthocyanin peaks by the AUC of all peaks in the 250-700 nm max-plot. Table 1 summarizes the purification conditions.

TABLE 1

Mobile phases[1] used to elute compounds of interest from the cartridges

| | Cartridges | | | |
|---|---|---|---|---|
| | Oasis® MCX | Sep-pak® $C_{18}$ | Sephadex® LH-20 | Oasis® HLB |
| Loading & washing | $H_2O$ | $H_2O$ | 20% MeOH | 15% MeOH |
| Phenol fraction | MeOH | EtOAc | $N/A^2$ | EtOAc |
| Anthocyanin fraction | 60%-100% MeOH with 1% $NH_4OH^3$ | MeOH | 70% MeOH | MeOH |
| Tannin fraction | N/A | N/A | MeOH and 70% acetone | N/A |

[1]0.1% TFA was added to all solvents except that in the original $C_{18}$ method 0.01% HCl was used to follow the reported literatures. TFA as a volatile acid effectively reduced the accumulation of acid after evaporation, and decreased the potential of affecting biological subjects.
[2]N/A, not available.
[3]This alkaline eluate was immediately mixed with an aliquot of formic acid to bring the pH to <2. Acidification must be prompt to prevent anthocyanin degradation.

Non-parametric Kruskal-Wallis test followed by Post-Hoc Dunnett's T3 multiple mean comparisons were conducted using SPSS (version 13) to detect significant differences between treatments. All fractions also were analyzed by a FTIR spectrometer for composition profiling using a protocol previously developed in our lab.

Results and Discussion

Figure 4A:
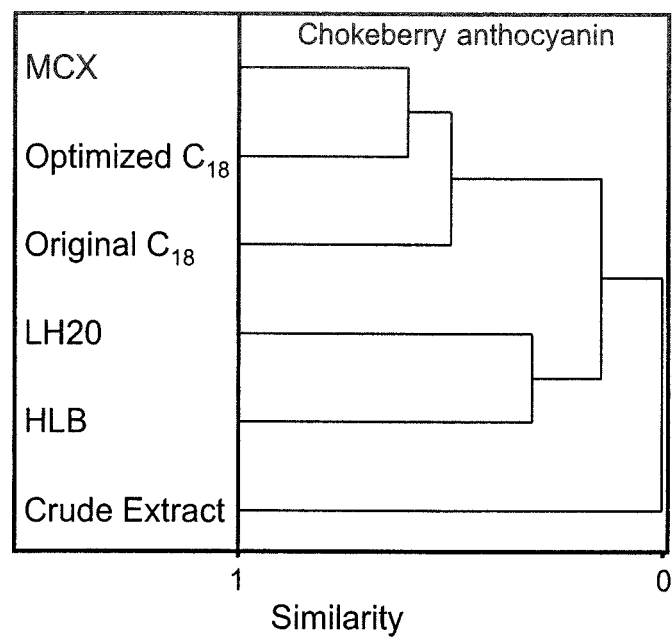
FIGS. 4A and 4B graphically illustrates decreasing similarity from the crude extract to the HLB, LH20, $C_{18}$, and MCX eluents for chokeberry anthocyanin and purple corn anthocyanin, as reported in the Examples.
Figure 4B:
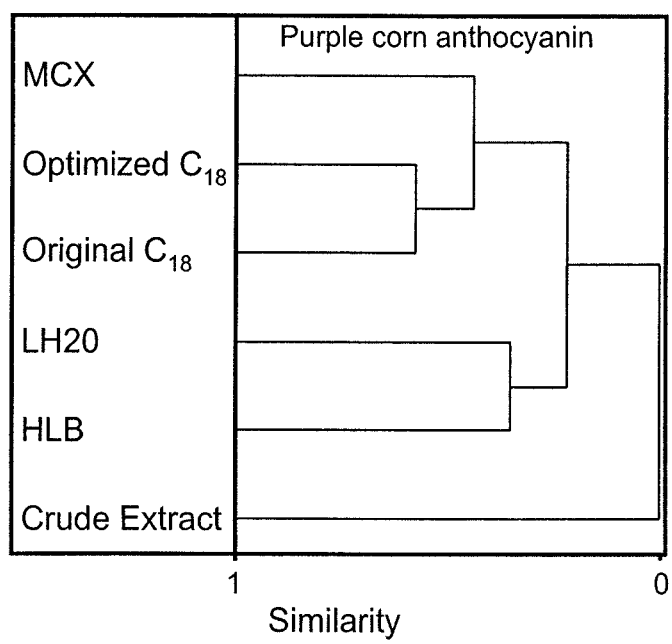

The disclosed separation technique initiated from the hypothesis that positively charged anthocyanin molecules (pKa ~2.6) at low pH (FIG. 4) would interact with a strong cation exchange sorbent; meanwhile, most other compounds without positive charges could be easily removed. However, cartridges relying on solely cation-exchange mechanism demonstrated poor binding to anthocyanins. The Oasis® MCX cartridge, originally designed for drug analysis, was packed with a mixed-mode resin combining both strong cation-exchange mechanism and reversed phase interaction, a mechanism commonly employed for isolation of anthocyanins (FIG. 4). To elute anthocyanins from the resin, $NH_4OH$ was selected to raise the mobile phase pH hence remove the positive charge on anthocyanin molecules. Meanwhile excessive $NH_4^+$ could compete with the cation binding sites on the resin to facilitate dissociation.

TABLE 2

Visually Observed Anthocyanin Color Loss

| | Cartridges | | | |
|---|---|---|---|---|
| | Oasis® MCX | Sep-Pak® $C_{18}$ | Sephadex® LH-20 | Oasis® HLB |
| Loading & washing | — | —[1] | + + | + |
| Phenol/tannin fraction | — | + | + | + |
| Residue on sorbent | + | — | + + | + + |

[1]—, not observable; +, slightly observed; ++, obvious.

The MCX and $C_{18}$ cartridges appeared to have unbiased selection on all anthocyanins, whereas the HLB and LH20 cartridges recovered the hydrophilic anthocyanins less efficiently. Visual observation (Table 2) revealed leaching of color into the aqueous washing solution in the case of HLB and LH20 cartridges, explaining the loss of hydrophilic anthocyanins. A special advantage of MCX was its strong retention of anthocyanins. This cartridge could load several folds more anthocyanins than others with similar weight of sorbents, and even in a methanol extract anthocyanins could directly bind to the MCX sorbent while all other methods require evaporating out the organic solvents, an extra step causing delays and possibly resulting in degradation.

Kruskal-Wallis test, a non-parametric analogue of ANOVA, was conducted on the purity and recovery data derived from the UV-Vis chromatogram, because the homogeneity of variance assumption was not met. The unequal variances indicated varied reproducibility of different cartridges. Post-hoc analysis determined that the MCX method resulted in significantly higher purity ($P<0.05$) of the anthocyanin fraction and significantly lower residue anthocyanin ($P<0.05$) in the phenol fraction than other methods (FIGS. 2 A and B). The recovery rates of the MCX method also were the highest or in par with the highest (FIGS. 2 C and D).

Figure 3:
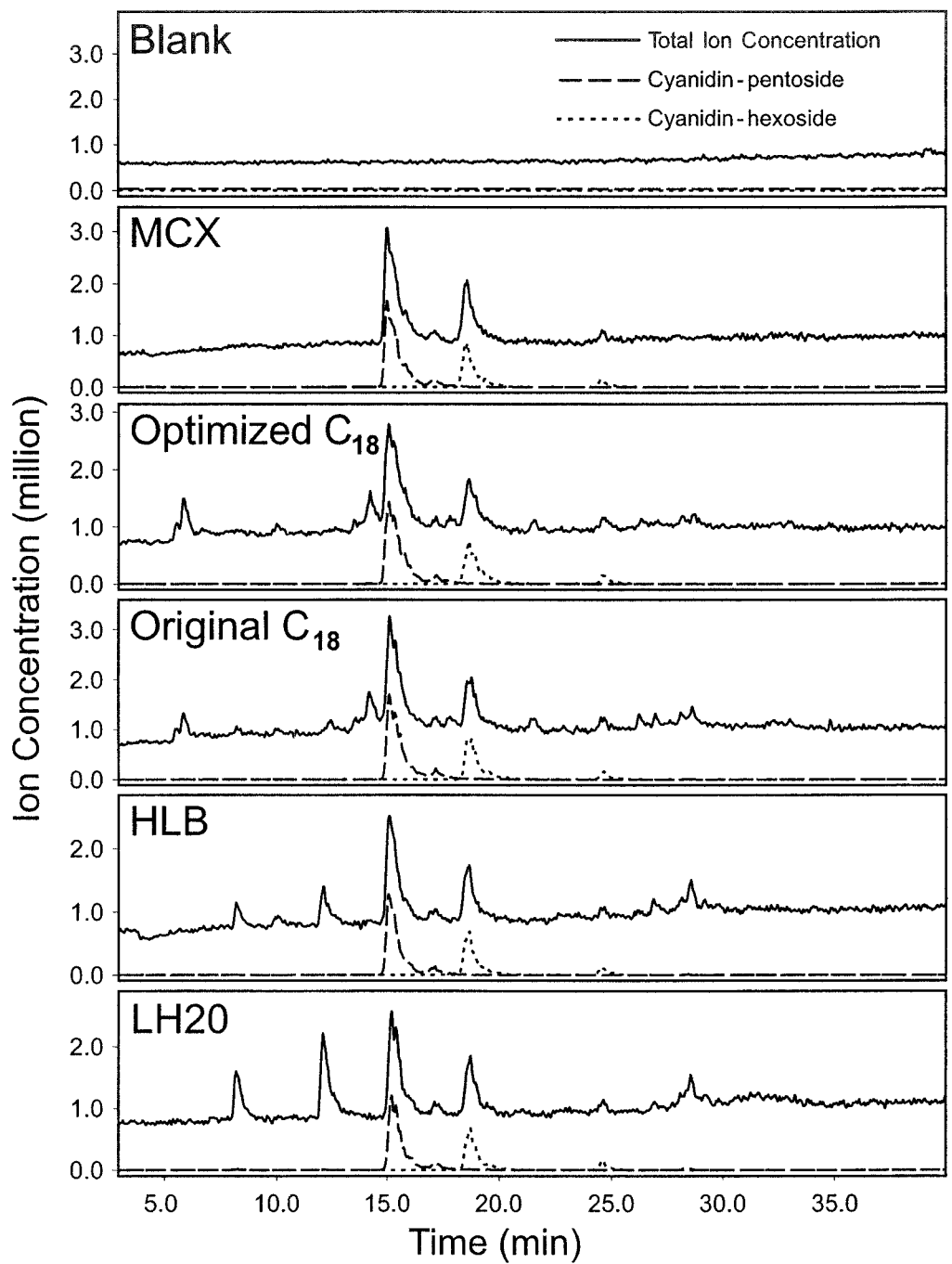
FIG. 3 graphically plots total ion concentration of the various fractionation cartridges recorded by a MS detector versus time, as reported in the Examples.

Purity is measured based on absorbance in the 250-700 nm range. Phenolic compounds and many other organic compounds belong to this class. However, this method has a limitation in that compounds without absorbance in the UV-visible range are not detectable. Therefore, two additional analytical methods were employed to confirm the calculated purity. Total ion concentration recorded by a MS detector showed only anthocyanin peaks for the MCX anthocyanin fraction (FIG. 3), indicating high purity; yet, multiple noise peaks were present with other isolation methods. Chemometric analysis of infrared spectra classified all the anthocyanin fractions (de-salted) with compositionally similar samples grouped close together. The decreasing similarity from the crude extract to the HLB, LH20, $C_{18}$, and MCX eluents indicated increasing purity (FIG. 4).

When eluting the anthocyanin fraction with alkaline solution, 60% and 100% methanol were used in the above example, but principally an aqueous methanol solution with 0 to 100% methanol content was capable of eluting anthocyanins. For highly hydrophilic anthocyanins, lower percentage of methanol may be preferred for more efficient elution.

Alternative Solvents and Chemicals:

Methanol, a solvent often used for anthocyanin extraction, was used to optimize the procedures. But to apply this method to prepare edible anthocyanins, a non-toxic solvent, such as, for example, ethanol, can be used. Ethanol displayed no significant difference regarding purity and recovery when tested. Different chemicals could be used to manipulate solvent pH as long as they provide a slightly basic pH and do not react with anthocyanins. Examples of these are, for example, ammonium, $K_2CO_3$ and $Na_2CO_3$, which all worked properly.

Additional Research:

Besides the chokeberry and purple corn already being elaborated, other common anthocyanin-rich fruits and vegetables were evaluated. Bilberry, black currant, blueberry, elderberry, purple carrot, and red cabbage anthocyanins were purified to above 99% purity (n=4). Black raspberry, strawberry, grape and radish anthocyanins were purified to 97.4%, 94.2%, 93.8% and 85.6% purities respectively. This method also may be used to achieve ultra high purity for many other anthocyanin-rich fruits and vegetables.

Radish extract, a mixture providing stable color and close hue to Red #40, was particularly studied with respect to removal of its strong adverse aroma. A blind test involving 12 subjects determined that the MCX method ($N_2CO_3$ solution) achieved significantly lower ($P=0.014$) odor than the $C_{18}$ method using LSD mean comparison following ANOVA. Higher anthocyanin purity (85.6%) obtained by the MCX method than the $C_{18}$ method (47.0%) adequately explained the difference of odor.

Sequential coupling of more than one type of resin was studied. As mentioned above, anthocyanins present in organic solvents can be directly loaded onto the MCX resin, and this makes it easy to directly load organic eluents from other resins. When black raspberry extract was sequentially purified by $C_{18}$ and MCX columns, the anthocyanin purity was successfully increased to almost 100%.

Sorbent Capacity

Sorbent capacity was determined using 2 different approaches. Chokeberry extract was used as representative source of anthocyanins to determine sorbent capacity. In a preliminary test, with equivalent amount of sorbent material and equal concentration of introduced chokeberry anthocyanins, the different sorbents were visually evaluated for their breaking-through volumes (after which red color leached out of the column). Then, the capacity of selected sorbents was further quantified by HPLC measurement (n=3). Sorbents were first saturated with excessive amounts of chokeberry anthocyanins, and the retained total anthocyanins were expressed as mg cyanidin-3-glucoside equivalent/g sorbent. The mass of total anthocyanins recovered was calculated based on a cyanidin-3-glucoside standard calibration curve ($R^2>0.99$).

Figure 1A:
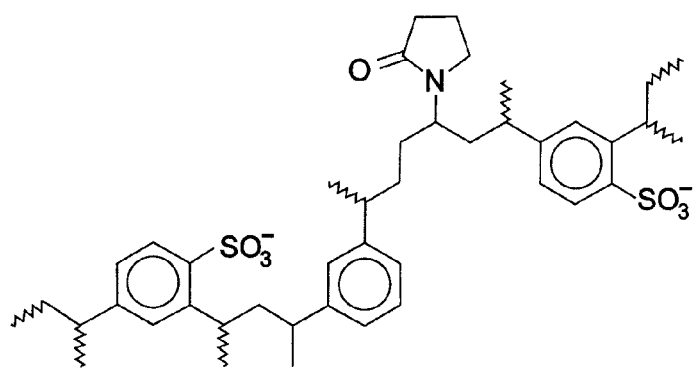
FIG. 1A is the chemical structure of modified divinylbenzene-vinylpyrrolidone copolymer with a hydrogen atom on benzene substituted by a sulfuric group.
Figure 2A:
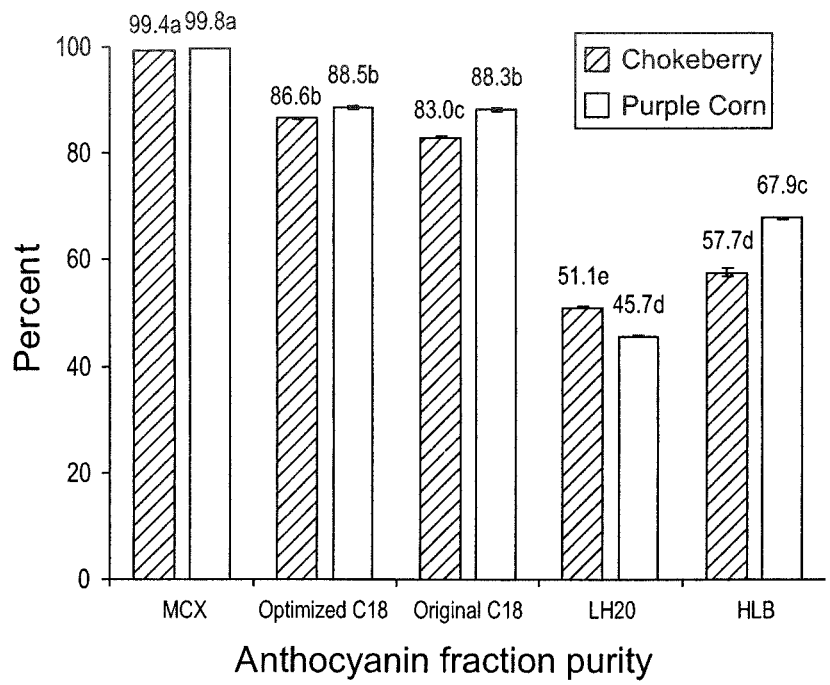
FIG. 2A graphically plots anthocyanin fraction purity of chokeberry and purple corn fractioned with different cartridge compositions, as reported in the Examples.
Figure 2B:
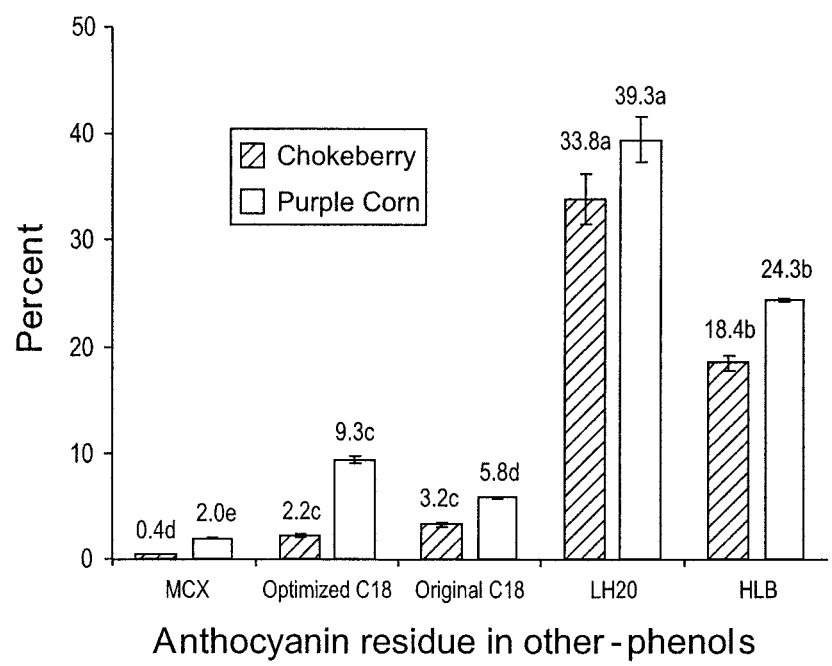
FIG. 2b graphically plots anthocyanin residue in other phenols for chokeberry and purple corn fractioned with different cartridge compositions, as reported in the Examples.
Figure 2C:
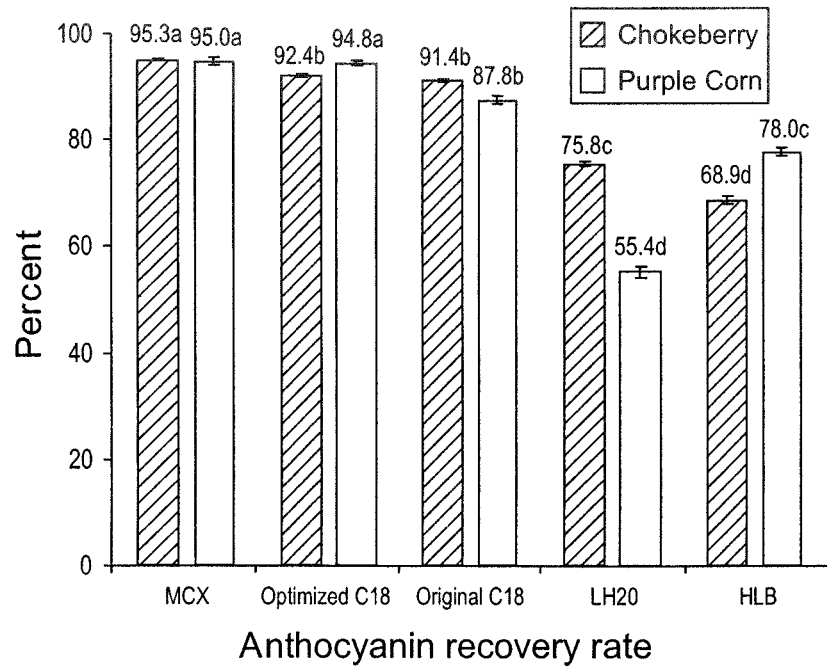
FIG. 2C graphically plots anthocyanin recovery rate for chokeberry and purple corn fractioned with different cartridge compositions, as reported in the Examples.
Figure 2D:
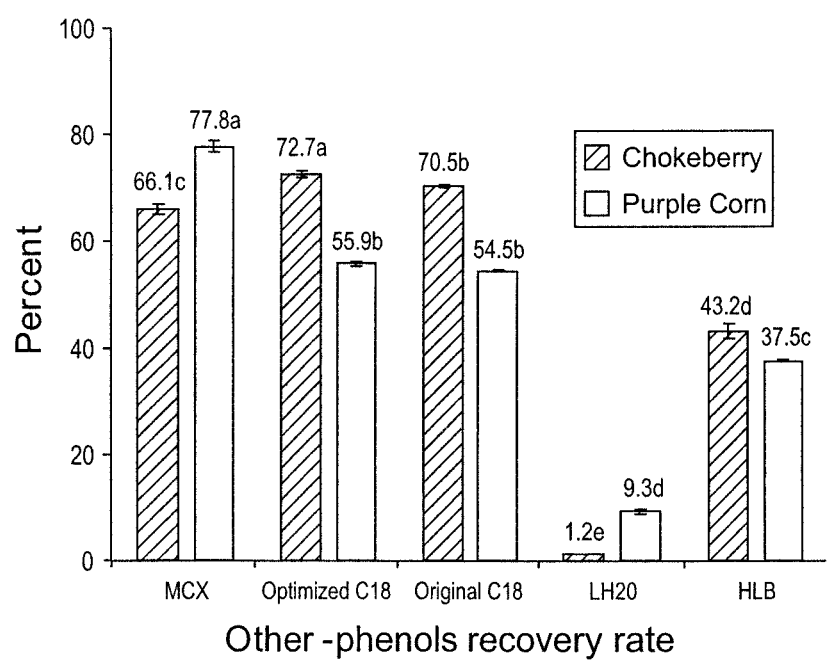
FIG. 2D graphically plots other phenols recovery rate for chokeberry and purple corn fractioned with different cartridge compositions, as reported in the Examples.

Visual observation revealed substantially higher breakthrough volumes by the MCX and $C_{18}$ sorbents than by the other two sorbents, suggesting their strong retention of anthocyanins. The difference in capacity clearly affected the yield of anthocyanins when equivalent volumes of sample were applied onto the sorbents (Table 2). Sorbent capacity was further quantified to be 45.8 mg and 19.0 mg cyanidin-3-glucoside equivalent/g sorbent for the MCX and $C_{18}$, respectively. Presumably, due to the additional ionic interaction, the MCX had stronger retention of anthocyanins than the $C_{18}$, and this high capacity resulted in less number of cycles per gram of end product, and meanwhile less use of organic solvents. Another advantage of this strong retention, which has been mentioned above, is that even methanolic extracts could be directly loaded onto the MCX sorbent and anthocyanins would not leach out. Enhanced dissociation of anthocyanins from MCX was observed as compared to the HLB sorbent (Table 2), which is based on the same type of hydrophobic backbone. This was probably attributed to the repelling forces between negatively charged anthocyanin molecules and the sulfonic groups on the MCX sorbent (FIG. 1).

Impact of Highly Alkaline Condition on Acylated Anthocyanins

It is noteworthy that strong alkaline conditions can favor dissociation of the organic acids from the sugar moieties (saponification) of acylated anthocyanins—mainly those with aliphatic acid acylations. Therefore, when acylated anthocyanins are eluted from the cartridge, the alkaline pH (9.5-10) may cause partial anthocyanin saponification, even if the eluted solution is immediately acidified. To prevent this problem, the use neutral or slightly alkaline pH is recommended to preserve anthocyanin profile when working with acylated anthocyanin sources. We further investigated less alkaline mobile phase (<pH 8.5) for eluting anthocyanins. Elution was accomplished, but the transition of anthocyanin color was slower and the elution required longer time to complete, reducing the efficiency of the process.

Extended Work

Anthocyanins from alternative edible sources that are not commercially applicable for food use as crude extract form also can be recovered. It is possible to use this mixed-mode cation exchange resin technology to remove adverse aroma and flavor from radish anthocyanins and remove toxic glycoalkaloid from eggplant skin and potato anthocyanins. Optimizing the pH of eluting solvents anthocyanins could further aid in separating positively charged interference compounds, such as, for example, nitro-containing odorants and glycoalkaloids with higher pKa (>6) than anthocyanins (<3). The polarity of eluting solvents, for example, using ethyl acetate and hexane, could be adjusted to help further optimize the disclosed method and remove more non-polar content, such as, for example, some aroma compounds in radish and polymeric tannins in purple corn and grape, which are extremely hard to be removed by any established methods Due to the neutralization of alkaline and acid, trace amount of salt is formed during the MCX purification procedure. The residual salt generally is not a concern in chemical and biological studies; however, in case that salts need to be removed, membrane technique or column separation technique, $C_{18}$ resin as an example, can be employed.

As noted above, the phenolics separated from the desired anthocyanin fraction represent an important class of compounds, also of interests for research and/or food applications. The phenolics fraction is recovered substantially free of anthocyanins. Thus, the reported purification method also produces substantially pure (I.e., free of anthocyanins) phenolics fraction.

CONCLUSION

An innovative mixed-mode cation exchange anthocyanin isolation method is disclosed herein. This method is superior to the commonly used methods regarding purity, recovery, sorbent capacity, low cost, and simplicity of the procedures. The resulted high purity anthocyanins could be advantageous in scientific studies, as well as food applications.

We claim:

1. A method for separating anthocyanins from plant tissue feedstock containing anthocyanins and phenolic mixtures, which comprises the sequential steps of:
   (a) contacting said feedstock with a mixed mode cation-exchange resin for a time period effective for said resin to selectively bind with said anthocyanins;
   (b) separating non-bound phenolic mixture from said resin;
   (c) subjecting bound resin to alkaline solvent wash to release said anthocyanins in an eluate;
   (d) mixing the eluate with an acid such that a resulting mixture has pH less than about pH 2; and
   (e) recovering, from the resulting mixture, anthocyanins having a purity of at least 85%.

2. The method of claim 1, wherein said anthocyanins are released by washing said bound resin with a solvent having a pH of between about 9.5 and about 10.

3. The method of claim 2, wherein said solvent is basified with one or more of ammonium, potassium carbonate, or sodium carbonate.

4. The method of claim 3, wherein said anthocyanins are released by washing said bound resin with the basified solvent being aqueous methanol, aqueous ethanol, hexane, or ethyl acetate.

5. The method of claim 3, wherein said anthocyanins are released by washing said bound resin with the basified solvent being aqueous methanol or aqueous ethanol.

6. The method of claim 1, wherein the feedstock comprises a liquid derived from a plant selected from one or more of the following: chokeberry, purple corn, bilberry, black currant, black raspberry, blueberry, elderberry, grape, radish, red cabbage, eggplant, potato, strawberry, or purple carrot.

7. The method of claim 1, wherein said mixed-mode cation-exchange resin comprises divinylbenzene-vinylpyrrolidone copolymer modified with a hydrogen atom on benzene substituted by a sulfuric group.

8. The method of claim 1, wherein the feedstock comprises acylated anthocyanin sources and wherein the alkaline solvent wash pH is between 7 and 8.5, thereby minimizing saponification.

9. The method of claim 1, wherein said plant tissue comprises fruits, vegetables, or flowers.

10. The method of claim 1, wherein the alkaline solvent wash comprises a food-grade solvent.

11. The method of claim 1, further comprising the step:
    evaporating the solvent from the resulting mixture.

12. The method of claim 1, further comprising:
    recovering, from the resulting mixture, anthocyanins having a purity of at least 99%.

13. The method of claim 1, further comprising:
    yielding, from the resulting mixture, at least 93% of the anthocyanins from the feedstock.

14. A method for purifying anthocyanins comprising sequentially:
    providing an anthocyanin-containing supernatant;
    adsorbing anthocyanins from the supernatant onto a resin under acid conditions;
    washing the resin with a first solvent;
    eluting the anthocyanins from the resin with a second solvent to produce an anthocyanin-rich eluate, wherein the second solvent is alkaline, wherein the second solvent is a food-grade solvent having pH between 7 and 8.5;
    mixing the eluate with an acid such that the resulting mixture has a pH of less than about 2; and
    recovering, from the resulting mixture, anthocyanins having a purity of at least 85%.

15. The method of claim 14, wherein the supernatant further comprises one or more of: tannin, non-anthocyanin phenolic, and glycoalkoloid.

* * * * *

UNITED STATES PATENT AND TRADEMARK OFFICE
CERTIFICATE OF CORRECTION

PATENT NO. : 8,575,334 B2  
APPLICATION NO. : 12/847106  
DATED : November 5, 2013  
INVENTOR(S) : Jian He and Maria Monica Giusti Page 1 of 1

It is certified that error appears in the above-identified patent and that said Letters Patent is hereby corrected as shown below:

In the Specification

Column 1, Line 12 add Government Support Clause "This invention was made with government support under grant number 2004-35503-15190 awarded by the National Institute of Food and Agriculture. The government has certain rights in the invention."

Signed and Sealed this  
Sixth Day of October, 2020

Andrei Iancu  
*Director of the United States Patent and Trademark Office*